(12) United States Patent
Ishikawa et al.

(10) Patent No.: US 10,093,617 B1
(45) Date of Patent: Oct. 9, 2018

(54) METHOD FOR PRODUCING 2-AMINO-4-SUBSTITUTED PHENOL

(71) Applicant: SUMITOMO CHEMICAL COMPANY, LIMITED, Tokyo (JP)

(72) Inventors: Junichi Ishikawa, Takarazuka (JP); Yuta Honda, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/765,351

(22) PCT Filed: Oct. 10, 2016

(86) PCT No.: PCT/JP2016/081220
§ 371 (c)(1),
(2) Date: Apr. 2, 2018

(87) PCT Pub. No.: WO2017/073468
PCT Pub. Date: May 4, 2017

(30) Foreign Application Priority Data

Oct. 30, 2015 (JP) .................................. 2015-214013

(51) Int. Cl.
C07C 315/04 (2006.01)
C07C 315/02 (2006.01)
C07C 317/36 (2006.01)

(52) U.S. Cl.
CPC .......... *C07C 315/02* (2013.01); *C07C 317/36* (2013.01)

(58) Field of Classification Search
CPC .... C07C 315/04; C07C 315/02; C07C 317/36
See application file for complete search history.

(56) References Cited

U.S. PATENT DOCUMENTS 6,005,008 A 12/1999 Widdowson et al.
9,615,580 B2 * 4/2017 Takahashi ............ C07D 263/57

FOREIGN PATENT DOCUMENTS

| JP | 11-503110 A | 3/1999 |
| JP | 2003-501459 A | 1/2003 |
| WO | WO 00/76495 A1 | 12/2000 |
| WO | WO 2014/104407 A1 | 7/2014 |

OTHER PUBLICATIONS

International Preliminary Report on Patentability issued in corresponding International Application No. PCT/JP2016/081220 dated May 1, 2018.
Fujiwara et al., "Practical and innate carbon-hydrogen functionalization of heterocycles", Nature, vol. 492, Dec. 6, 2012, pp. 95-100.
International Search Report issued in PCT/JP2016/081220 (PCT/ISA/210), dated Nov. 29, 2016.
Zilla et al., "A convergent synthesis of alkyne-azide cycloaddition derivatives of 4-α,β-2-propyne podophyllotoxin depicting potent cytotoxic activity", European Journal of Medicinal Chemistry, vol. 77, 2014, pp. 47-55.

* cited by examiner

*Primary Examiner* — Jafar F Parsa
(74) *Attorney, Agent, or Firm* — Birch, Stewart, Kolasch & Birch, LLP

(57) ABSTRACT

A compound represented by formula (3):

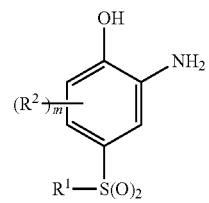

(3)

(wherein $R^1$ represents a C1-C6 alkyl group optionally having one or more halogen atoms, $R^2$ represents a C1-C6 alkyl group, and m represents an integer of 0 to 3)
can be produced by reacting a C1-C6 alkanesulfinic acid salt optionally having one or more halogen atoms with a compound represented by formula (2):

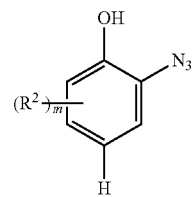

(2)

(wherein $R^2$ and m are as defined above)
in the presence of a protonic acid.

8 Claims, No Drawings

METHOD FOR PRODUCING 2-AMINO-4-SUBSTITUTED PHENOL

TECHNICAL FIELD

The present invention directs to a method for producing 2-amino-4-substituted phenol useful as an intermediate for production of a pesticide.

BACKGROUND ART

2-Amino-4-substituted phenol is useful as an intermediate for production of a pesticide. In addition, a method is a known in which 4-trifluoromethylsulfonylphenol is nitrated, and then reduced to produce 2-amino-4-trifluoromethylsulfonylphenol (see WO 2014/104407).

SUMMARY OF THE INVENTION

The present invention provides a novel method for producing 2-amino-4-substituted phenol.
The present invention is as follows.
[1] A method for producing a compound represented by formula (3):

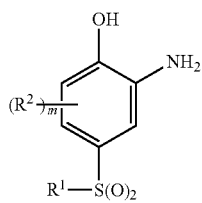

(wherein $R^1$ represents a C1-C6 alkyl group optionally having one or more halogen atoms, $R^2$ represents a C1-C6 alkyl group, and m represents an integer of 0 to 3) (hereinafter, referred to as Compound (3)), the method comprising reacting a C1-C6 alkanesulfinic acid salt optionally having one or more halogen atoms with a compound represented by formula (2):

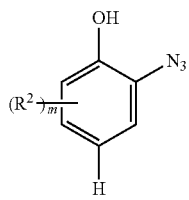

(wherein $R^2$ and m are as defined above)
(hereinafter, referred to as Compound (2)) in the presence of a protonic acid.
[2] The production method according to [1], wherein the protonic acid is an organic sulfonic acid compound.
[3] The production method according to [1], wherein the protonic acid is methanesulfonic acid.
[4] The production method according to any one of [1] to [3], wherein $R^1$ is a C1-C3 perfluoroalkyl group.
[5] The production method according to any one of [1] to [4], wherein m is 0.
[6] The production method according to any one of [1] to [5], wherein the C1-C6 alkanesulfinic acid salt optionally having one or more halogen atoms is a compound represented by formula (1a$^1$):

$$R^1S(O)OM^1 \qquad (1a^1)$$

(wherein $R^1$ is as defined above, and $M^1$ represents sodium or potassium).
[7] The production method according to [6], wherein $R^1$ is a trifluoromethyl group.
[8] A method for producing a compound represented by formula (3):

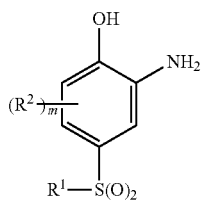

(wherein $R^1$, $R^2$ and m are as defined above),
the method comprising
a step of diazotizing a compound represented by formula (4):

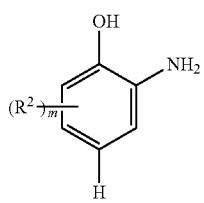

(wherein $R^2$ and m are as defined above),
and then azidating the diazotized product to produce a compound represented by formula (2):

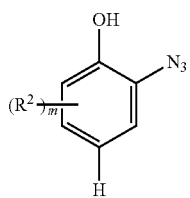

(wherein $R^2$ and m are as defined above); and
a step of reacting the compound represented by formula (2) with a C1-C6 alkanesulfinic acid salt optionally having one or more halogen atoms in the presence of a protonic acid to produce the compound represented by formula (3).

MODE FOR CARRYING OUT THE INVENTION

Hereinafter, the present invention will be described. Examples of the C1-C6 alkyl group of $R^1$ and $R^2$ include alkyl groups having 1 to 6 carbon atoms, such as a methyl group, an ethyl group, a propyl group, an isopropyl group, a butyl group, a sec-butyl group, a tert-butyl group, a pentyl group, a 2-pentyl group, a neopentyl group, a 4-methyl-2-pentyl group, a hexyl group and a 3-methylpentyl group, with C1-C3 alkyl groups being preferable.

The halogen atom is a fluorine atom, a chlorine atom, a bromine atom or an iodine atom.

The alkali metal is lithium, sodium, potassium, rubidium or cesium.

Examples of the organic sulfonic acid compound which is a protonic acid include methanesulfonic acid, trifluoromethanesulfonic acid, benzenesulfonic acid and p-toluenesulfonic acid.

A preferred embodiment of $R^1$ is a C1-C3 perfluoroalkyl group, and specific examples thereof include a trifluoromethyl group, a pentafluoroethyl group and a heptafluoropropyl group.

Compound (3) can be obtained by reacting a C1-C6 alkanesulfinic acid salt, which optionally has one or more halogen atoms, with Compound (2) in the presence of a protonic acid.

In the C1-C6 alkanesulfinic acid salt optionally having one or more halogen atoms, the salt is normally an alkali metal salt or a zinc salt.

The alkali metal salt of the C1-C6 alkanesulfinic acid salt optionally having one or more halogen atoms is represented by formula (1a):

(wherein $R^1$ is as defined above, and M represents an alkali metal), and the zinc salt is represented by formula (1b):

(wherein $R^1$ is as defined above).

Examples of the sulfinic acid salt represented by formula (1a) include sodium methanesulfinate, sodium ethanesulfinate, sodium propanesulfinate, sodium isopropanesulfinate, sodium butanesulfinate, sodium sec-butanesulfinate, sodium tert-butanesulfinate, sodium trifluoromethanesulfinate, potassium trifluoromethanesulfinate, sodium pentafluoroethanesulfinate, potassium pentafluoroethanesulfinate, sodium heptafluoropropanesulfinate, potassium heptafluoropropanesulfinate, sodium nonafluorobutanesulfinate and sodium tridecafluorohexanesulfinate. The sulfinic acid salt represented by formula (1a) can be obtained by purchasing a commercially available product, or performing synthesis in accordance with, for example, the method described in WO2011/108622.

Examples of the sulfinic acid salt represented by formula (1b) include zinc bis(trifluoromethanesulfinate), zinc bis(pentafluoroethanesulfinate) and zinc bis(tridecafluorohexanesulfinate). The sulfinic acid salt represented by formula (1b) can be obtained by purchasing a commercially available product, or performing synthesis in accordance with, for example, the method described in Nature (London, United Kingdom) (2012), 492 (7427), 95-99.).

The C1-C6 alkanesulfinic acid salt optionally having one or more halogen atoms is preferably a compound represented by formula (1a¹), and $R^1$ is more preferably a trifluoromethyl group, most preferably sodium trifluoromethanesulfinate or potassium trifluoromethanesulfinate.

Examples of Compound (2) include 2-azidophenol, 2-azido-3-methylphenol, 2-azido-5-methylphenol, 2-azido-6-methylphenol, 2-azido-3-ethylphenol, 2-azido-5-ethylphenol and 2-azido-6-ethylphenol. The compound (2) can be produced from a compound represented by formula (4):

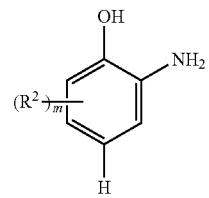

(wherein $R^2$ and m are as defined above) using a method as described later.

Examples of Compound (3) include 2-amino-4-methanesulfonylphenol, 2-amino-3-methyl-4-methanesulfonylphenol, 2-amino-4-ethanesulfonylphenol, 2-amino-4-trifluoromethanesulfonylphenol, 2-amino-3-methyl-4-trifluoromethanesulfonylphenol, 2-amino-5-methyl-4-trifluoromethanesulfonylphenol, 2-amino-6-methyl-4-trifluoromethanesulfonylphenol, 2-amino-3-ethyl-4-trifluoromethanesulfonylphenol, 2-amino-5-ethyl-4-trifluoromethanesulfonylphenol, 2-amino-6-ethyl-4-trifluoromethanesulfonylphenol and 2-amino-4-pentafluoroethanesulfonylphenol.

The reaction of the C1-C6 alkanesulfinic acid salt, which optionally has one or more halogen atoms, with Compound (2) is carried out in the presence of a protonic acid.

Examples of the protonic acid to be used in the reaction include inorganic acids such as hydrochloric acid and sulfuric acid; organic sulfonic acid compounds such as methanesulfonic acid, trifluoromethanesulfonic acid, benzenesulfonic acid and p-toluenesulfonic acid; and organic carboxylic acid compounds such as acetic acid and trifluoroacetic acid. Among them, organic sulfonic acid compounds are preferable, with methanesulfonic acid being more preferable.

The amount of the protonic acid to be used is normally 1 mol to 10 mol based on 1 mol of Compound (2).

The reaction is normally carried out in a solvent. Examples of the solvent include aromatic hydrocarbons such as toluene, xylene, cumene and tetralin; aromatic halogenated hydrocarbons such as monochlorobenzene and o-dichlorobenzene; hydrocarbons such as hexane, heptane, octane, nonane and cyclohexane; sulfur-containing compounds such as dimethyl sulfoxide and sulfolane; ethers such as tetrahydrofuran, 2-methyltetrahydrofuran, cyclopentyl methyl ether, tert-butyl methyl ether, 1,2-dimethoxyethane and diglyme; organic carboxylic acids such as acetic acid, propionic acid, butyric acid and ethylhexanoic acid; amides such as N,N-dimethylacetamide, N,N-dimethylformamide and N-methylpyrrolidone; nitriles such as acetonitrile and propionitrile; esters such as methyl acetate and ethyl acetate; ketones such as acetone, methyl ethyl ketone and methyl isobutyl ketone; alcohols such as methanol, ethanol and propanol; and mixtures thereof. Among these, ketones and ethers are preferable.

The amount of the solvent to be used is normally 1 to 100 times, preferably 1 to 10 times the amount of Compound (2) in terms of a weight.

The C1-C6 alkanesulfinic acid salt optionally having one or more halogen atoms is normally used in an amount of 1 mol to 5 mol based on 1 mol of Compound (2).

The reaction temperature is within a range from room temperature to 200° C.

The reaction time is within a range from 10 minutes to 24 hours.

The reaction is normally carried out by mixing the C1-C6 alkanesulfinic acid salt optionally having one or more halogen atoms, Compound (2) and a protonic acid.

Examples of the mixing method include:

Method 1) in which the C1-C6 alkanesulfinic acid salt optionally having one or more halogen atoms, Compound (2) and a protonic acid are added in a reaction vessel, and mixed;

Method 2) in which the C1-C6 alkanesulfinic acid salt optionally having one or more halogen atoms, and a protonic acid are added in a reaction vessel, and mixed, and Compound (2) is then added dropwise to the resulting mixture;

Method 3) in which the C1-C6 alkanesulfinic acid salt optionally having one or more halogen atoms is added in a reaction vessel, and Compound (2) and a protonic acid are then simultaneously added dropwise; and Method 4) in which the C1-C6 alkanesulfinic acid salt optionally having one or more halogen atoms is added in a reaction vessel, a part of the protonic acid is then added dropwise, and subsequently Compound (2) and the remainder of the protonic acid are simultaneously added dropwise.

Method 2), Method 3) and Method 4) in which Compound (2) is added dropwise are preferable from the viewpoint of safety, and Method 4) is preferable from the viewpoint of a yield.

Compound (2) is normally diluted with a solvent, and used for mixing.

Preferably, Compound (2) is subjected to a drying procedure, and used for the reaction.

Preferably, the drying procedure of Compound (2) is performed by a method in which a solvent is distilled off from a mixture of Compound (2) and the solvent.

In addition, it is preferable to add a drying agent in a reaction system for carrying out the reaction under a dried condition. Examples of the drying agent to be added in the reaction system include anhydrous magnesium sulfate and anhydrous sodium sulfate.

After completion of the reaction, Compound (3) can be isolated by subjecting the reaction mixture to concentration under reduced pressure, crystallization or the like. Compound (3) can be isolated by distilling off the solvent from the reaction mixture, then adding water, methanol or the like, performing a treatment with an adsorbent such as activated carbon, and then concentrating the mixture under reduced pressure. The resulting Compound (3) can be further purified by recrystallization, extraction, chromatography or the like.

Compound (2) can be produced in the following manner: Compound (4) is reacted with a nitrous acid salt in an acidic aqueous solution to be diazotized, so that a compound represented by formula (5):

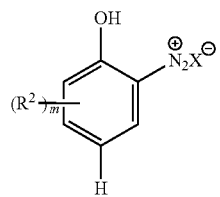

(5)

(where $X^-$ represents an anion, and $R^2$ and m are as defined above) is produced, and an alkali metal azide such as sodium azide or potassium azide is added to the compound represented by formula (5) to azidate the compound represented by formula (5).

Examples of the acid to be used for the acidic aqueous solution include inorganic acids such as hydrochloric acid and sulfuric acid. The use amount of the acid is normally 1 to 15 mol based on 1 mol of Compound (4)

Examples of the nitrous acid salt to be used include sodium nitrite and potassium nitrite. The use amount of the nitrous acid salt is normally 1 to 5 mol based on 1 mol of Compound (4).

The amount of the alkali metal azide to be used is normally 1 to 5 mol based on 1 mol of Compound (4).

The reaction temperature for diazotization and azidation is normally within a range of $-10°$ C. to $100°$ C. The reaction time for diazotization is within a range of 10 minutes to 24 hours. The reaction time for azidation is within the range of 10 minutes to 48 hours.

After completion of the reaction, Compound (2) can be isolated by extracting the reaction product with an organic solvent or the like, and concentrating the extract.

Examples of the organic solvent to be used for extraction include aromatic hydrocarbons such as toluene, xylene, cumene and tetralin; aromatic halogenated hydrocarbons such as monochlorobenzene and o-dichlorobenzene; ethers such as cyclopentyl methyl ether and tert-butyl methyl ether; nitriles such as propylnitrile; esters such as methyl acetate and ethyl acetate; ketones such as methyl isobutyl ketone; and mixtures thereof.

Compound (2) may be used in the next step as it is without being isolated. Here, Compound (2) may be subjected to a drying procedure.

EXAMPLES

Hereinafter, the present invention will be described by way of examples, but the present invention is not limited to these examples.

Measurement Conditions
    Measurement: High performance liquid chromatography
    Mobile phase liquid A: 0.1% phosphoric acid aqueous solution, liquid B: acetonitrile
    Column: SUMIPAX (registered trademark) ODS Z-CLUE (manufactured by Sumika Chemical Analysis Service, Ltd.) inner diameter: 4.6 mm, length: 100 mm, particle diameter: 3 µm
    Column temperature: $40°$ C.
    Flow rate: 1.0 mL/min
    UV wavelength: 250 nm
    Injection volume: 10 µl
    Internal standard substance: acetanilide
    Time program

| Time (minutes) | Mobile phase liquid B (%) |
| --- | --- |
| 0 | 10 |
| 40 | 90 |
| 50 | 90 |
| 50.1 | 10 |
| 60 | 10 |

Example 1-1

45.9 mmol (5 g) of 2-aminophenol, 25 g of 35% hydrochloric acid and 25 g of water were mixed while being cooled in an ice water bath under a nitrogen atmosphere. To this mixture, a mixture of 45.9 mmol (3.17 g) of sodium nitrite and 2.5 g of water was added dropwise, and the mixture was then stirred for 30 minutes while being cooled in an ice water bath. Next, 55.0 mmol (3.58 g) of sodium azide was added, the ice water bath was then removed, the mixture was stirred for 1 hour, and disappearance of 2-aminophenol as a raw material was confirmed by high performance liquid chromatography.

The reaction mixture was extracted with 50 g of ethyl acetate per extraction, the extraction was repeated 3 times, and the resulting organic layers were combined, concentrated under reduced pressure, and then subjected to column purification to obtain 3.44 g of 2-azidophenol (yield: 55%).

$^1$H-NMR (CDCl$_3$) δ: 6.9-7.0 (m, 2H), 7.0-7.1 (m, 2H), 7.70 (s, 1H),

MS(FD) m/z=135

Example 1-2

0.5 mmol (0.078 g) of sodium trifluoromethanesulfinate, 0.25 mmol (0.034 g) of 2-azidophenol and 0.1 mL of 98% sulfuric acid were added to 1 mL of ethanol, and the mixture was heated and stirred at 100° C. for 3 hours. Using an internal standard analysis method by high performance liquid chromatography, generation of 2-amino-4-trifluoromethanesulfonylphenol with a yield of 33% was confirmed.

Examples 1-3

A reaction was carried out in accordance with the method described in Example 1-2 using a solvent, a sulfinic acid salt and a protonic acid as described in [Table 1] below. The results are shown below.

In the table in this specification, CF$_3$S(O)ONa represents sodium trifluoromethanesulfinate, CF$_3$S(O)OK represents potassium trifluoromethanesulfinate, and (CF$_3$S(O)O)$_2$Zn represents zinc bis(trifluoromethanesulfinate).

TABLE 1

| Solvent | Sulfinic acid salt | Protonic acid (use amount) | Yield |
|---|---|---|---|
| Ethanol | CF$_3$S(O)ONa | 36% concentrated hydrochloric acid (0.1 mL) | 21% |
| n-Butanol | CF$_3$S(O)ONa | Methanesulfonic acid (0.6 mmol) | 39% |
| Acetonitrile | CF$_3$S(O)ONa | Methanesulfonic acid (0.6 mmol) | 17% |
| Propionitrile | CF$_3$S(O)ONa | Methanesulfonic acid (0.6 mmol) | 29% |
| Toluene | CF$_3$S(O)ONa | Methanesulfonic acid (0.6 mmol) | 30% |
| 2-Ethylhexanoic acid | CF$_3$S(O)ONa | Methanesulfonic acid (0.6 mmol) | 34% |
| tert-Butyl methyl ether | CF$_3$S(O)ONa | Methanesulfonic acid (0.6 mmol) | 37% |
| Dimethoxyethane | CF$_3$S(O)ONa | Methanesulfonic acid (0.6 mmol) | 51% |
| Dimethoxyethane | CF$_3$S(O)ONa | Methanesulfonic acid (1.1 mmol) | 49% |
| Cyclopentyl methyl ether | CF$_3$S(O)ONa | Methanesulfonic acid (1.1 mmol) | 37% |
| Dimethoxyethane | CF$_3$S(O)OK | Methanesulfonic acid (1.1 mmol) | 50% |
| Dimethoxyethane | (CF$_3$S(O)O)$_2$Zn | Methanesulfonic acid (1.1 mmol) | 49% |

Example 2

7.40 mmol (1.0 g) of 2-azidophenol, 8.14 mmol (1.27 g) of sodium trifluoromethanesulfinate and 16.3 mmol (1.57 g) of methanesulfonic acid were added to 10 g of 1,2-dimethoxyethane under a nitrogen atmosphere, and the mixture was stirred at 90° C. for 6 hours. A part of the resulting product was collected, and analyzed using an internal standard analysis method by high performance liquid chromatography, and the result showed that the yield of 2-amino-4-trifluoromethanesulfonylphenol was 69%.

The reaction mixture was cooled to room temperature, 20 g of water and 20 g of tert-butyl methyl ether were added to the reaction mixture, the mixture was subjected to an extraction operation, and the fractionated organic layer was concentrated under reduced pressure to obtain 1.70 g of 2-amino-4-trifluoromethanesulfonylphenol. A part of the resulting product was collected, and analyzed using an internal standard analysis method by high performance liquid chromatography, and the result showed that the yield of 2-amino-4-trifluoromethanesulfonylphenol was 66%.

Example 3

22.9 mmol (2.5 g) of 2-aminophenol, 5.0 g of 35% hydrochloric acid and 20 g of water were mixed while being cooled in an ice water bath under a nitrogen atmosphere. To this mixture, a mixture of 25.2 mmol (1.74 g) of sodium nitrite and 2.5 g of water was added dropwise, and the mixture was then stirred for 30 minutes while being cooled in an ice water bath. Next, 27.5 mmol (1.79 g) of sodium azide was added, the ice water bath was then removed, and the mixture was stirred for 1 hour.

20 g of ethyl acetate was added to the reaction mixture, the mixture was subjected to an extraction operation, and the fractionated organic layer was concentrated under reduced pressure to obtain 2-azidophenol.

The total amount of 2-azidophenol obtained as described above was dissolved in 25 g of 1,2-dimethoxyethane, a liquid obtained by mixing 22.9 mmol (3.58 g) of sodium trifluoromethanesulfinate and 45.9 mmol (4.41 g) of methanesulfonic acid was then added, and the mixture was stirred at 90° C. for 6 hours. A part of the resulting product was collected, and analyzed using an internal standard analysis method by high performance liquid chromatography, and the result showed that the yield of 2-amino-4-trifluoromethanesulfonylphenol was 60%.

The reaction mixture was cooled to room temperature, 100 g of water and 100 g of ethyl acetate were added, the mixture was subjected to an extraction operation, and the fractionated organic layer was concentrated under reduced pressure to obtain 5.03 g of 2-amino-4-trifluoromethanesulfonylphenol.

A part of the resulting product was collected, and analyzed using an internal standard analysis method by high performance liquid chromatography, and the result showed that the yield of 2-amino-4-trifluoromethanesulfonylphenol was 59% (in terms of 2-aminophenol).

Example 4

22.9 mmol (2.5 g) of 2-aminophenol, 5.0 g of 35% hydrochloric acid and 20 g of water were mixed while being cooled in an ice water bath under a nitrogen atmosphere. To this mixture, a mixture of 25.2 mmol (1.74 g) of sodium nitrite and 2.5 g of water was added dropwise, the mixture was then stirred for 30 minutes while being cooled with ice, 27.5 mmol (1.79 g) of sodium azide was then added, and the mixture was then stirred for 1 hour.

20 g of ethyl acetate was added to the reaction mixture, the mixture was subjected to an extraction operation, and the fractionated organic layer was concentrated under reduced pressure to obtain 2-azidophenol.

22.9 mmol (3.58 g) of sodium trifluoromethanesulfinate and 45.9 mmol (4.41 g) of methanesulfonic acid were added to 15 g of 1,2-dimethoxyethane, the mixture was heated to 90° C., and a mixture of the total amount of 2-azidophenol obtained as described above and 10 g of 1,2-dimethoxyethane was then added dropwise over 6 hours.

After completion of dropwise addition, the reaction mixture was cooled to room temperature, 100 g of water and 100 g of ethyl acetate were added, the mixture was subjected to an extraction operation, and the fractionated organic layer was concentrated under reduced pressure to obtain 6.28 g of 2-amino-4-trifluoromethanesulfonylphenol. A part of the resulting product was collected, and analyzed using an internal standard analysis method by high performance liquid chromatography, and the result showed that the yield of 2-amino-4-trifluoromethanesulfonylphenol was 57% (in terms of 2-aminophenol).

Example 5

183.2 mmol (20.00 g) of 2-aminophenol, 40.86 g of 35% hydrochloric acid and 100.00 g of water were mixed under a nitrogen atmosphere, and the mixture was cooled to −2° C. To this mixture, 32.88 g of a 40% sodium nitrite aqueous solution was added dropwise over 2 hours, and the mixture was then stirred at −2° C. for 30 minutes. Next, 40.00 g of methyl isobutyl ketone was added to the reaction mixture, the mixture was mixed, 46.81 g of a 28% sodium azide aqueous solution was added dropwise over 3 hours, and the mixture was then stirred at −2° C. for 1 hour. After completion of the reaction, the mixture was separated to obtain 67.08 g of a methyl isobutyl ketone solution of 2-azidophenol.

25.9 mmol (4.06 g) of sodium trifluoromethanesulfinate and 17.51 g of methyl isobutyl ketone were mixed under a nitrogen atmosphere, and to the mixture was added dropwise 26.9 mmol (2.59 g) of methanesulfonic acid. This mixture was heated to 40° C., and 9.50 g of the methyl isobutyl ketone solution of 2-azidophenol, which was obtained in an amount of 67.08 g as described above, and 51.5 mmol (4.95 g) of methanesulfonic acid were then simultaneously added dropwise over 5 hours.

After completion of dropwise addition, the reaction mixture was stirred at 40° C. for 5 hours, then cooled to room temperature, and washed with 29.14 g of a 8% sodium hydroxide aqueous solution added to the mixture. The mixture was separated to obtain a methyl isobutyl ketone solution of 2-amino-4-trifluoromethanesulfonylphenol. A part of the resulting product was collected, and analyzed using an internal standard analysis method by high performance liquid chromatography, and the result showed that the yield of 2-amino-4-trifluoromethanesulfonylphenol was 69% (in terms of 2-azidophenol).

Example 6

274.9 mmol (30.00 g) of 2-aminophenol, 61.28 g of 35% hydrochloric acid and 150.00 g of water were mixed under a nitrogen atmosphere, and the mixture was cooled to −2° C. To this mixture, 49.32 g of a 40% sodium nitrite aqueous solution was added dropwise over 2 hours, and the mixture was then stirred at −2° C. for 30 minutes.

60.00 g of methyl isobutyl ketone was added to the reaction mixture, the mixture was mixed, 70.21 g of a 28% sodium azide aqueous solution was added dropwise over 3 hours, and the mixture was then stirred at −2° C. for 1 hour. After completion of the reaction, the mixture was separated to obtain 98.64 g of a methyl isobutyl ketone solution of 2-azidophenol.

Next, 45.00 g of methyl isobutyl ketone was added to the methyl isobutyl ketone solution of 2-azidophenol obtained as described above, and the solvent was distilled off under a reduced pressure condition until the weight of the distillate was 45.00 g, so that 98.64 g of a dried methyl isobutyl ketone solution of 2-azidophenol was obtained.

5.55 mmol (0.87 g) of sodium trifluoromethanesulfinate, 0.31 mmol (37.5 mg) of anhydrous magnesium sulfate and 3.75 g of methyl isobutyl ketone were mixed under a nitrogen atmosphere, and to the mixture was added dropwise 5.55 mmol (0.53 g) of methanesulfonic acid. This mixture was heated to 40° C., and 1.99 g of the above-mentioned dried methyl isobutyl ketone solution of 2-azidophenol, which was obtained in an amount of 98.64 g, and 11.1 mmol (1.07 g) of methanesulfonic acid were then simultaneously added dropwise over 5 hours.

After completion of dropwise addition, the reaction mixture was stirred at 40° C. for 5 hours, then cooled to room temperature, and washed with 5.58 g of a 8% sodium hydroxide aqueous solution added to the mixture. The mixture was separated to obtain a methyl isobutyl ketone solution of 2-amino-4-trifluoromethanesulfonylphenol. A part of the resulting product was collected, and analyzed using an internal standard analysis method by high performance liquid chromatography, and the result showed that the yield of 2-amino-4-trifluoromethanesulfonylphenol was 81% (in terms of 2-azidophenol).

Example 7

229.1 mmol (25.00 g) of 2-aminophenol, 51.07 g of 35% hydrochloric acid and 125.00 g of water were mixed under a nitrogen atmosphere, and the mixture was cooled to −2° C. To this mixture, 41.10 g of a 40% sodium nitrite aqueous solution was added dropwise over 2 hours, and the mixture was then stirred at −2° C. for 30 minutes.

50.00 g of methyl isobutyl ketone was added to the reaction mixture, the mixture was mixed, 58.51 g of a 28% sodium azide aqueous solution was added dropwise over 3 hours, and the mixture was then stirred at −2° C. for 1 hour. After completion of the reaction, the mixture was separated to obtain 82.42 g of a methyl isobutyl ketone solution of 2-azidophenol.

Next, 37.50 g of methyl isobutyl ketone was added to the methyl isobutyl ketone solution of 2-azidophenol obtained as described above, and the solvent was distilled off under a reduced pressure condition until the weight of the distillate was 37.50 g, so that 82.42 g of a dried methyl isobutyl ketone solution of 2-azidophenol was obtained.

148.0 mmol (23.10 g) of sodium trifluoromethanesulfinate, 8.3 mmol (1.00 g) of anhydrous magnesium sulfate and 100.0 g of methyl isobutyl ketone were mixed under a nitrogen atmosphere, and to the mixture was added dropwise 148.0 mmol (14.22 g) of methanesulfonic acid. This mixture was heated to 40° C., and 53.25 g of the above-mentioned dehydrated methyl isobutyl ketone solution of 2-azidophenol, which was obtained in an amount of 82.42 g, and 296.0 mmol (28.45 g) of methanesulfonic acid were then simultaneously added dropwise over 5 hours.

After completion of dropwise addition, the reaction mixture was stirred at 40° C. for 5 hours, then cooled to room temperature, and washed with 148.01 g of a 8% sodium hydroxide aqueous solution added to the mixture, and the mixture was separated to obtain 210.60 g of a methyl isobutyl ketone solution of 2-amino-4-trifluoromethanesulfonylphenol. Apart of the resulting product was collected, and analyzed using an internal standard analysis method by high performance liquid chromatography, and the result showed that the yield of 2-amino-4-trifluoromethanesulfonylphenol was 76% (in terms of 2-azidophenol).

38.82 g of the resulting methyl isobutyl ketone solution of 2-amino-4-trifluoromethanesulfonylphenol was concentrated under reduced pressure to distill off methyl isobutyl ketone. 7.50 g of water and 7.50 g of methanol were added to the residues, the mixture was subjected to an adsorption treatment with activated carbon, the solvent was distilled off under reduced pressure, and 10.00 g of water and 5.00 g of methanol were then added to perform cooling crystallization, so that 4.75 g of 2-amino-4-trifluoromethanesulfonylphenol was obtained. A part of the resulting product was collected, and analyzed using an internal standard analysis method by high performance liquid chromatography, and the result showed that the yield of 2-amino-4-trifluoromethanesulfonylphenol was 72% (in terms of 2-azidophenol).

INDUSTRIAL APPLICABILITY

According to the present invention, 2-amino-4-substituted phenol useful as an intermediate for production of a pesticide can be produced.

The invention claimed is:

1. A method for producing a compound represented by formula (3):

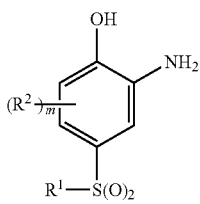
(3)

wherein $R^1$ represents a C1-C6 alkyl group optionally having one or more halogen atoms, $R^2$ represents a C1-C6 alkyl group, and m represents an integer of 0 to 3, the method comprising reacting a C1-C6 alkanesulfinic acid salt optionally having one or more halogen atoms with a compound represented by formula (2):

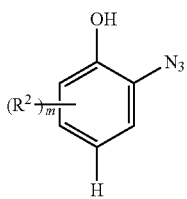
(2)

wherein $R^2$ and m are as defined above, in the presence of a protonic acid.

2. The production method according to claim 1, wherein the protonic acid is an organic sulfonic acid compound.

3. The production method according to claim 1, wherein the protonic acid is methanesulfonic acid.

4. The production method according to claim 1, wherein $R^1$ is a C1-C3 perfluoroalkyl group.

5. The production method according to claim 1, wherein m is 0.

6. The production method according to claim 1, wherein the C1-C6 alkanesulfinic acid salt optionally having one or more halogen atoms is a compound represented by formula ($1a^1$):

$$R^1S(O)OM^1 \qquad (1a^1)$$

wherein $R^1$ is as defined above, and $M^1$ represents sodium or potassium.

7. The production method according to claim 6, wherein $R^1$ is a trifluoromethyl group.

8. A method for producing a compound represented by formula (3) as set forth in claim 1, the method comprising a step of diazotizing a compound represented by formula (4):

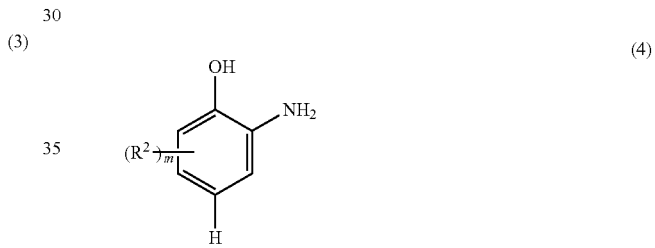
(4)

wherein $R^2$ represents a C1-C6 alkyl group, and m represents an integer of 0 to 3, and then azidating the diazotized product to produce a compound represented by formula (2):

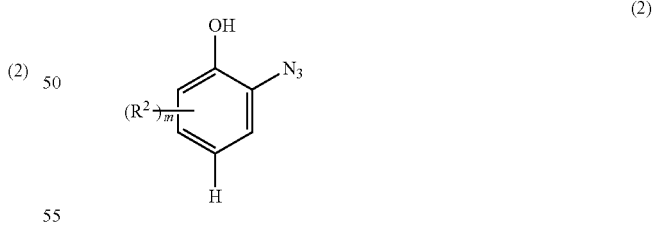
(2)

wherein $R^2$ and m are as defined above.

* * * * *